United States Patent
Omar et al.

(10) Patent No.: US 10,668,020 B1
(45) Date of Patent: Jun. 2, 2020

(54) PULLULAN BASED VINPOCETINE TABLETS, LYOPLANT-TABS, AS A BUCCAL SOLID DOSAGE FORM

(71) Applicant: King Abdulaziz University, Jeddah (SA)

(72) Inventors: Abdelsattar M. Omar, Jeddah (SA); Tarek A. Ahmed, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/690,662

(22) Filed: Nov. 21, 2019

(51) Int. Cl.
*A61K 9/20* (2006.01)
*A61K 31/4375* (2006.01)
*A61K 9/00* (2006.01)

(52) U.S. Cl.
CPC .......... *A61K 9/2054* (2013.01); *A61K 9/2018* (2013.01); *A61K 9/2095* (2013.01); *A61K 31/4375* (2013.01); *A61K 9/006* (2013.01)

(58) Field of Classification Search
None
See application file for complete search history.

(56) References Cited

FOREIGN PATENT DOCUMENTS

| CN | 102283798 A | * 12/2011 | ............... A61K 9/00 |
| CN | 102283798 A | * 12/2011 | ............... A61K 9/00 |
| CN | 102100676 B | * 4/2012 | ............... A61K 9/20 |
| CN | 102327208 B | * 10/2012 | ............... A61K 9/00 |
| CN | 102327208 B | * 10/2012 | ............... A61K 9/00 |
| JP | 63250318 A | * 10/1988 | ............... A61K 9/00 |

OTHER PUBLICATIONS

Kharshoum et al., International Journal of Drug Delivery (2013), 5(2), pp. 167-176.*

* cited by examiner

*Primary Examiner* — Brian J Davis
(74) *Attorney, Agent, or Firm* — W&C IP

(57) ABSTRACT

Solid dosage pullulan-based buccal tablets containing a polyvinyl pyrrolidone and vinpocetine (e.g., lyophilized polyvinyl pyrrolidone vinyl acetate and vinpocetine), when administered via the buccal mucosa, provide increased bioavailability of the active agent. The formulations may be used to treat a variety of indications for which vinpocetine has been shown to have beneficial activity, and have particular utility in the treatment of cerebral degenerative diseases.

14 Claims, 6 Drawing Sheets

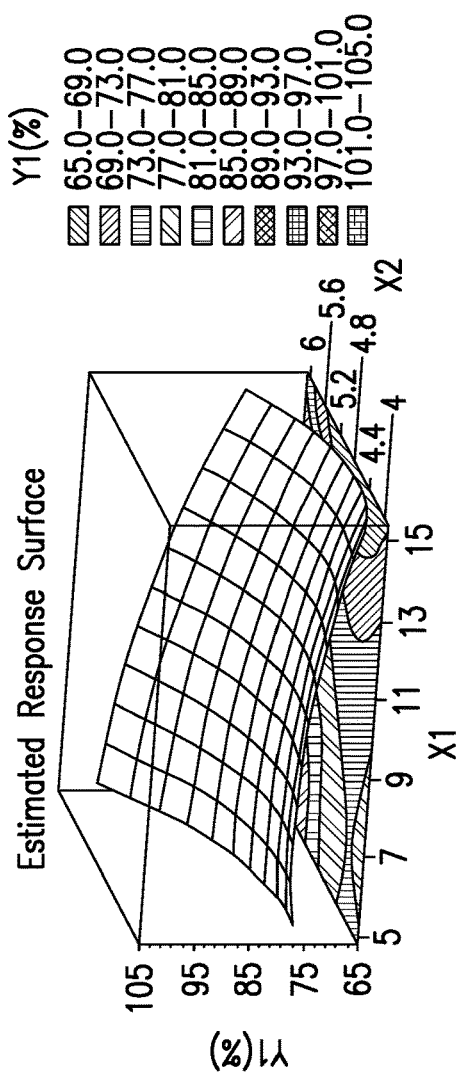
FIG.5A
FIG.5B
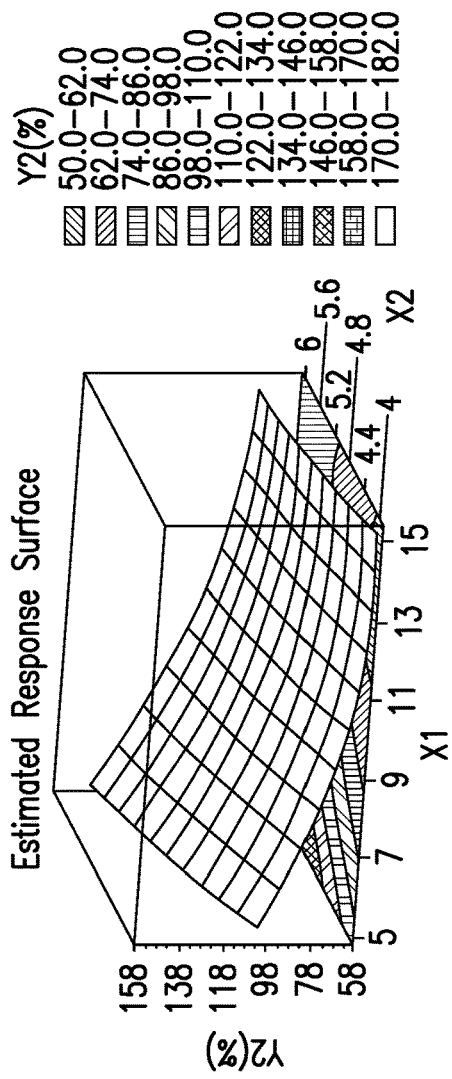
FIG.5C
FIG.5D

PULLULAN BASED VINPOCETINE TABLETS, LYOPLANT-TABS, AS A BUCCAL SOLID DOSAGE FORM

FIELD OF THE INVENTION

The invention is generally related to development of pullulan-based lyophilized solid dosage form containing physically modified vinpocetine. In particular, the invention provides tablets containing lyophilized binary system of vinpocetine and polyvinyl pyrrolidone vinyl acetate suitable for buccal delivery of vinpocetine in a highly bioavailable form.

BACKGROUND OF THE INVENTION

Different pharmaceutical formulation strategies have been used to enhance the bioavailability of drugs that are suffering from poor aqueous solubility. These include; size reduction by nano-sizing and micronization, use of cosolvents and surfactants, solid dispersion, and inclusion complexation. Moreover, formation of colloidal drug delivery systems such as solid lipid nanoparticles (NP), polymeric based NP, lipid based NP, microemulsion formation and self-microemulsifying drug delivery systems have attracted increasing attention. The solid dispersion technique, first introduced in the early 1970s, is the distribution of a hydrophobic drug(s) in and around a hydrophilic polymer(s) in the solid state. Melting (fusion), solvent evaporation, melt-extrusion and super critical anti-solvent processes are commonly used to prepare solid dispersions. Polyvinyl pyrrolidone (PVP) namely; poly-[1-(2-oxo-1-pyrrolidinyl)-ethylene], is a water-soluble polymer that has been utilized in solid dispersion preparations to improve solubility and dissolution of many water insoluble drugs.

Vinpocetine (VPN) is a derivative of the alkaloid vincamine which has been reported to have vasodilator, anti-ischemic, anti-convulsant, anti-inflammatory and neuroprotective activity. It is a weak basic drug (pKa=7.31) with a limited water solubility of 2.4 gig/mL. The main mechanism of drug action is attributed to inhibition of the enzyme phosphodiesterase (PDE) type-1 that results in increase in the level of 3,4-dihydroxyphenylacetic acid (DOPAC), a metabolic breakdown product of dopamine, which selectively enhances the brain circulation and oxygen utilization without significant modification in systemic circulation parameters. It facilitates blood flow redistribution towards ischemic areas, and enhances cerebral circulation and oxygen utilization. The major concerns about VPN are the poor aqueous solubility, short elimination half-life (1-2 h), and the extensive first pass metabolism (75% metabolism in liver) that limit the drug bioavailability. VPN is currently administered as an oral tablet containing 5 mg of the drug but with poor oral bioavailability. Several drug delivery systems have been employed in an attempt to overcome VPN delivery drawbacks, such as mixed polymeric micelles, solid lipid nanoparticles and self-microemulsifying drug delivery systems. However, none of these has been very successful and it would be highly beneficial to have available improved formulations that enhance the drug's aqueous solubility and bioavailability for the effective treatment of cerebral degenerative diseases.

SUMMARY OF THE INVENTION

Disclosed herein are pharmaceutical compositions of vinpocetine which exhibit enhanced aqueous solubility and, because they are delivered via the buccal mucosa, they avoid extensive first pass metabolism and thus display increased bioavailability. In particular, the pharmaceutical compositions are a binary (two-component) system comprising vinpocetine (VPN) and at least one polyvinyl pyrrolidone (PVP), both of which are lyophilized. In some aspects, the PVP is polyvinyl pyrrolidone vinyl acetate (PVP VA). In further aspects, pullulan is included as a new filler for tablet formulation. The buccal route of administration offers improved bioavailability and fast onset of action when compared to orally administered drugs. These advantages are attributed to avoidance of the first pass metabolism since the drug does not go through the gastrointestinal system. In this route, the drug is held in the cheek, diffuses through the oral mouth mucosal tissues ("buccal mucosa") and enters the blood stream directly. Product stability, drug wetting and solubility are also generally increased in buccal formulations as is the avoidance of high force of impaction used in direct compression techniques used to manufacture tablets for oral delivery.

An embodiment of the invention is to use pullulan as a filler for a tablet suitable for buccal delivery of an active agent to a human or mammal subject. In a particular embodiment, pullulan is used as a filler for a tablet that contains a binary system of vinpocetine and polyvinyl pyrrolidone vinyl acetate. Pullulan is the main component used in the preparation of the tablets, and the tablets produced are sometimes referred to herein as pullulan-based lyophilized tablets. In still other particular embodiments, the invention provides a method for treating cerebral degenerative diseases such as Parkinson's disease, Alzheimer's disease, dementia, etc., which includes administering through the buccal cavity of a human or mammal subject a pullulan-based lyophilized tablet containing a physically modified vinpocetine binary system (e.g., vinpocetine and polyvinyl pyrrolidone). By physically modified vinpocetine binary system we mean that a complex has developed between vinpocetine and polyvinyl pyrrolidone (PVP VA64 in some embodiments). This complex is not formed by a chemical interaction, rather, is formed by a physical interaction.

DESCRIPTION OF THE DRAWINGS

FIG. 5A-D. Standardized Pareto charts and estimated response surface plots for the effect of the studied factors on Y1 (A and B) and Y2 (C and D).

DETAILED DESCRIPTION

Figures 1A, 1B:
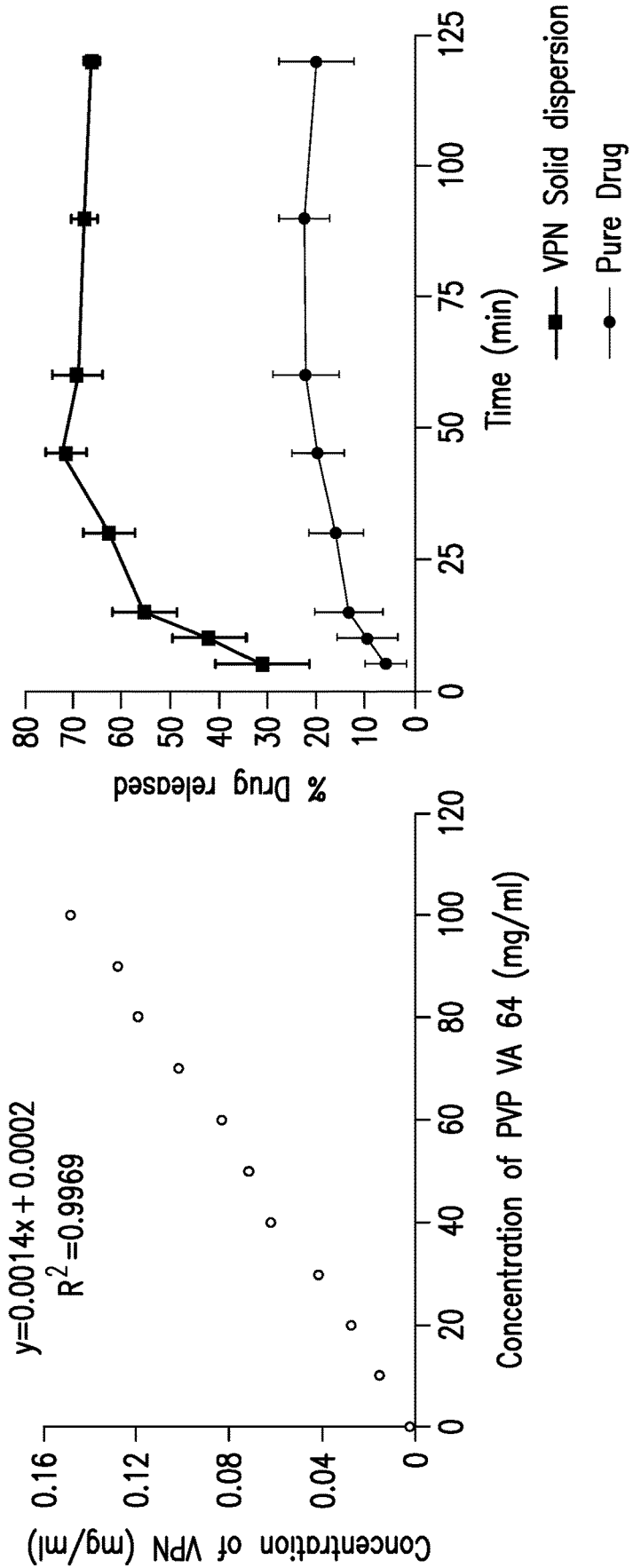
FIG. 1A-B. Phase solubility study diagram of VPN in aqueous solution of PVP-VA64 (A), and dissolution profile of VPN solid dispersion and pure drug (B).

Vinpocetine (VPN) has vasodilator, anti-ischemic, anti-convulsant, anti-inflammatory, and neuroprotective activity.

However, VPN is characterized by poor aqueous solubility, extensive first pass metabolism and limited bioavailability for effective treatment. For example, in the present disclosure, the solubility of VPN in water at 25° C. was found to be only 2.31 µg/mL. Accordingly, VPN is considered a practically water insoluble drug and the delivery of pharmaceutically effective amounts is problematic. The present invention overcomes this problem by providing buccal-deliverable solid dosage formulations of VPN with improved bioavailability. Methods of making the formulations and using them to treat a variety of cerebrovascular and other disorders are also provided.

To develop the formulations, VPN was combined with polyvinyl pyrrolidone (PVP) as a hydrophilic carrier to improve the solubility of the drug. The formulary compositions provided herein thus include a "binary" (two component) system comprising polyvinyl pyrrolidone and vinpocetine (PVP-VPN). The PVP-VPN binary systems described herein increase the solubility of VPN and its permeation across the buccal mucosa, thereby advantageously increasing the bioavailability of the cerebrovascular disorder drug.

Without being bound by theory, it is believed that enhancement of the drug solubility following complexation with PVPs can be attributed to conversion of the drug from the crystalline into the amorphous state, dispersion of the drug particles into the hydrophilic PVPs large surface area with subsequent enhancement in drug wettability, and a decrease in the drug particles tendency for aggregation and agglomeration.

Abbreviations

DOPAC: 3,4-dihydroxyphenylacetic acid
HPMC: hydroxylpropyl methylcellulose
NP: nanoparticles
PDE: phosphodiesterase
PVP: polyvinyl pyrrolidone
PVP-K25: Polyvinyl pyrrolidone, with an average molecular weight of 24,000 (K25)
PVP-K30: Polyvinyl pyrrolidone, with an average molecular weight of 44,000 (K30)
PVP-K90: Polyvinyl pyrrolidone, with an average molecular weight of 360,000 (K90)
PVP-VA64: polyvinyl pyrrolidone vinyl acetate
PVP-PXLUSP32: Polyvinyl pyrrolidone Polyplasdone XL United States Pharmacopeia 32 VPN: vinpocetine In some embodiments, the PVP is selected from one or more different grades, including but not limited to: PVP-K25, PVP-K30, PVP-K90, PVPVA64 and/or PVP-PXLUSP32, and mixtures thereof. In general, the PVP has a molecular weight in the range of 25,000 to 3,000,000. Drug to polymer ratios were studied to evaluate the effect of polymer concentration on drug solubility. The results indicated that drug solubility was augmented as the concentration of the polymer was increased, an effect which could be attributed to uniform distribution of VPN on the polymer surface. Accordingly, in preferred embodiments, the ratio of drug-to-polymer is from about 0.5:1 to about 1:5, for example, about 0.5:1, 1:1, 1:2, 1:3, 1:4 or 1:5, such as 1:1, 1:2, 1:3 or 1:4.

In a preferred embodiment, the polyvinyl pyrrolidone is polyvinyl pyrrolidone vinyl acetate (PVPVA64). In a further preferred embodiment, the VPN-to-PVPVA64 ratio is 1:4. As shown in the Examples section below, PVP-VA64 was superior to all the studied carriers with respect to enhancing the solubility and solubilization efficiency of VPN, following production by either the solvent evaporation or the lyophilization method. Without being bound by theory, this behavior may be attributed to the presence of the vinyl acetate group, which increases the polymer surface area and may facilitate more physical attraction between the carbonyl group of the vinyl acetate and the drug amino group.

In one embodiment, the VPN in the form of a PVP-VPN binary system, preferably a PVP-VA64-VPN binary system, enhances permeation of VPN across mouth mucosal tissues to increase drug bioavailability and therapeutic response.

Compositions

In one embodiment, buccal tablets of VPN are prepared by mixing a lyophilized PVP-VPN binary system with one or more excipients, e.g. a PVP-VA64-VPN binary system. An excipient is generally present in an amount of from about 0.5 to about 100% of the total weight of the final tablet, e.g. about 0.5, 1.0, 1.5, 2.0, 2.5, 3.0, 3.5, 4.0 4.5, 5.0, 5.5, 6.0, 6.5, 7.0, 7.5, 8.0, 8.5, 9.0, 9.5 or 10%. As is understood by those of skill in the art, some excipients have two or more functions, e.g. xylitol can serve as both a sweetener and a binder. The buccal table of VPN is generally obtained by freeze-drying a solution of the binary mixture and a plurality of excipients.

The excipients are selected from binders, fillers, sweeteners, swelling-aid polymers, lubricants, disintegrants or the mixture thereof. According to this embodiment, binders are selected from group comprising hydroxylpropyl cellulose, hydroxypropyl methyl cellulose, methyl cellulose, carboxymethyl cellulose, polyethylene glycol, polyvinyl alcohol, polyvinyl acetate, polyvinylpyrrolidone, sugars, glycose syrups, natural gums, guar gum, tragachanti gum, pregelatinized starch, gelatins, pullulan, agar, alginate, sodium algynates, glycyrrhizin, polymetacrylates, collagen, alginate, sodium alginate, hyaluronic acid, pectin, carrageenan, carbomer, poloxamer, polyacrylamide, aluminum hydroxide, benthonite, laponite, cetostearyl alcohol, polyoxyethylene-alkyl ethers, acacia mucilage, polydextrose, polyethylene oxide, xylitol, sucrose stearate or mixtures thereof. In some aspects, the binders are pullulan and hydroxylpropyl methylcellulose (HPMC).

Suitable fillers are selected from group comprising microcrystalline cellulose, lactose monohydrate, starch, mannitol, dibasic calcium phosphate, tribasic calcium phosphate, trehalose, isomalt, sodium carbonate, sodium bicarbonate, calcium carbonate or mixtures thereof.

Sweetening agents in the taste-masked pharmaceutical formulation, as recited herein, include a combination of a) at least one sugar or a sugar alcohol; and b) at least one artificial sweetener. Representative examples of sugars include glucose, fructose, invert sugar, sucrose, maltose, xylose, ribose, mannose, corn syrup solids, and mixtures thereof. The sugar alcohol includes xylitol, mannitol, sorbitol, and combinations thereof. The artificial sweeteners that may be used in the present invention include aspartame, cyclamates, saccharin, saccharin sodium, acesulfame-K, sucralose or combinations thereof. In some aspects, the sweeteners are aspartame and xylitol.

Suitable disintegrants are selected from the group comprising croscarmellose sodium, pregelatinized starch, crospovidone, sodium starch glycolate, low-substituted hydroxypropyl cellulose, polyvinylpyrrolidone, hydroxylpropyl methyl cellulose, carboxy methyl cellulose calcium, sodium carboxy methyl cellulose, magnesium aluminum silica, sodium dodecyl sulphate, calcium silicate or mixtures thereof.

In a preferred embodiment, the buccal tablets are prepared from a lyophilized binary system of VPN and PVP-VA64, and the tablet excipients are selected from binders, fillers, sweeteners, swelling-aid polymers, lubricants, disintegrants, and mixtures thereof.

In some aspects, the PCP-VPN buccal tablets also include pullulan, e.g. as a binder. Pullulan is a naturally occurring linear homopolysaccharide of glucose composed of maltotriose units that is obtained from starch by the fungus *Aureobasidium pullulans*. Pullulan based preparations readily dissolve in water, and, when delivered orally, immediately melt in the mouth. Pullulan is advantageously of natural origin, is non-genetically modified, and meets the requirements for consumers who prefer products that are GRAS (generally regarded as safe), and/or certified as Halal, kosher, vegan, etc. In fact, pullulan is the only plant derived polymer that meets the requirements for the "made with organic ingredients" label language in the United States.

Prior to this invention, no pullulan-based tablets are available in the market, under clinical trials, or have been mentioned in the literature. We have optimized the amount of pullulan in the developed tablets. Pullulan concentrations of 5%-15% were studied. It will be understood that the present formulations may additionally contain ingredients typically found in tablets intended for buccal administration, such as one or more of diluents, lubricants, glidants, disintegrants, coloring agents, flavoring agents, etc. Furthermore, the data below demonstrates that pullulan can be a suitable filler for any active agent, not simply the PVP-VPN binary system.

Methods of Preparation

In some aspects, the VPN polymeric solid dispersions are prepared by mixing VPN into a solution of polyvinyl pyrrolidone in 10% aqueous acetic acid, followed by solvent evaporation or lyophilization to yield a dry product. The results of the equilibrium solubility and solubility enhancement ratio revealed that lyophilization was superior to the solvent evaporation technique. Thus, generally the formulations disclosed herein are made by lyophilization and comprise lyophilized VPN and PVP. However, in some embodiments, the VPN and PVP binary system may be prepared using procedures other than lyophilization, e.g., freeze drying, solvent evaporation, etc.

When pullulan is present in the product, in some aspects, the pullulan may be provided in an aqueous solution (e.g. about 5-15% pullulan, such as about 5, 6, 7, 8, 9, 10, 12, 13, 14 or 15% by weight) and the VPN alone or a binary system of the drug and one or more PVPs are added to the solution, as dry ingredients, and optionally other tablet ingredients may be added. The VPN and PVP may be a lyophilized mixture prior to addition. However, other alternatives include: mixing one or more of pullulan, VPN and at least one PVP to form a dry mixture and dissolving the dry mixture in a suitable solvent (e.g. water, 10% acetic acid, etc.), etc., e.g. followed by lyophilization. In addition, one or more excipients as listed above may be included, e.g. in a mixture with the VPN and PVP prior to or after lyophilization, or mixed with the pullulan (if present), etc. The order of mixing is not necessarily crucial, as long as the final solution contains all the intended ingredients in a soluble form, and the final mixture is suitable for lyophilization and formation of a suitable solid dosage form, e.g. a buccal tablet.

In some aspects, buccal tablets of VPN are prepared by mixing a lyophilized binary system of PVP-VPN with excipients, and forming the mixture into tablets. Alternatively, the buccal tablets are obtained by freeze-drying a mixture of the binary system and excipients, and forming the freeze-dried mixture into tablets.

In some aspects, the buccal VPN tablets (also referred to herein as "lyo-plant" tablets) are prepared according to steps which comprise:
dissolving pullulan in water;
dispersing a quantity of lyophilized binary system of VPN, HPMC, aspartame, xylitol and PLASDONE™ XL (1-ethenylpyrrolidin-2-one) in the solution of pullulan; and
freeze-drying the mixture.

In some aspects,
the concentration of the aqueous pullulan solution is 5%, 10% or 15% w/v,
HPMC is present in a concentration of about 2% w/v,
aspartame is present in a concentration of about 0.125% w/v,
xylitol is present in a concentration of about 1.6% w/v, and
PLASDONE™ XL is present at a concentration of in the range of 4% to 6% w/v, such as 4.0%, 4.25%, 4.5%, 4.75%, 5.0%, 5.25%, 5.5%, 5.75% or 6%.

In some aspects, the binary system is prepared by lyophilizing a mixture of vinpocetine and polyvinyl pyrroline in a ratio of VPN:PVP of 1:1, 1:2 or 1:4, wherein preferably the polyvinyl pyrrolidone is polyvinyl pyrrolidone vinyl acetate.

In some aspects, the tablets are formed by, prior to freeze-drying, pouring the mixture into an empty pocket of a blister pack. However, those of skill in the art will recognize that other methods of forming the tablets may also be used, e.g. pressing, molding, extruding, etc. The tablets may be made by conventional techniques, including wet, dry or fluid-bed granulation methods, or direct compression. Preferably, the tablets are lyophilized.

Characteristics of the Buccal Tablets

In some embodiment, the lyoplant-tabs have a thickness of about 3.50 to 5.50 mm, such as about 3.5, 3.73, 4.0, 4.25, 4.50, 4.75, 5.0 or 5.50 mm.

In some embodiment, the lyoplant-tabs have a weight of about 105 to 180 mg, such as about 105, 110, 115, 120, 125, 130, 135, 140, 145, 150, 155, 160, 165, 170, 175 or 180 mg.

In some embodiment, the friability is in a range from 0.046 to 0.560% which is less than 1%. The wetting time is in a range from 4.33±0.22 to 14.51±1.57 minutes, while the drug content is in a range of 98.04±0.34 to 102.9±0.21%.

Methods of Using the Compositions

The disclosure also provides methods of treating neurodegenerative diseases (e.g. reducing the rate of cognitive decline) by administering the VPV-PVP-VPN compositions described herein. Examples of such diseases include but are not limited to various forms of cognitive decline and dementia such as Alzheimer's disease. However, other diseases and conditions have also been treated or suggested for treatment such as: age-related macular degeneration (AMD); reduction of the build-up of calcium around the joints in people with kidney failure who require hemodialysis, improving memory in healthy volunteers, reduction of brain damage due to acute ischemic stroke, tinnitus, bed-wetting and related urine control problems, motion sickness, symptoms of menopause, seizures, chronic fatigue syndrome (CFS), and generally for cognitive protective and as an anti-aging agent.

The methods generally comprise a step of administering, to a mammal (e.g., human, etc.) in need thereof, a therapeutically efficacious or effective amount of the formulations disclosed herein. In some aspects, the step of administering is conducted by bringing a PVP-VPN combination as described herein, e.g. a buccal tablet, into contact with the oral mucosa of the subject, for example, by inserting the tablet into the mouth, such as against the inner mucosa of the wall of the cheek, on the tongue or under the tongue. As the tablet remains in place, it disintegrates and releases the active agent, VPN, across the mucous membrane and directly into the blood stream of the subject. It is noted that in some cases, the subject may also purposefully or inadvertently chew the tablet; however, any of the composition that remains in the contact with the oral mucosa will function to deliver VPN to the circulatory system.

Also encompassed herein are methods of inhibiting the enzyme phosphodiesterase (PDE) type-1 in a subject in need thereof, and/or increasing in the level of 3,4-dihydroxyphenylacetic acid (DOPAC) in a subject in need thereof, by administering to the subject a PVP-VPN formulation for buccal delivery, as described above. Similarly, also encompassed are methods of selectively enhancing brain (cerebral) circulation and oxygen utilization (without significant modification in systemic circulation parameters) and/or facilitating blood flow redistribution towards ischemic areas by administering to the subject a PVP-VPN combination, designed for buccal administration, by administering the buccal tablets in a manner such as that described above.

Since the present formulations exhibit higher bioavailability compared to prior art VPN compositions and delivery methods, the amount of VPN that is administered per dose may be less than that required in the prior art, or administration may be less frequent. Currently, the amount of drug that is administered is typically in the daily dose range of from about 15 to about 60 mg (such as about 15, 20, 25, 30, 35, 40, 45, 50, 55 or 60 mg) total, taken as lower doses multiple times per day, e.g. 1, 2 3, or 4 times per day, and typically 3 times a day with meals. When taken multiple times per day, the dose may be, e.g., from 5 to 20 mg (such as about 5, 10, 15 or 20 mg per dose, 3 times per day). Higher doses in the range of e.g. 30-45 mg may be useful for promoting cognition and memory formation in otherwise healthy persons.

For the improved formulations described herein, the doses may be reduced, e.g. daily dose range of from about 3 to about 30 mg (such as about 3, 6, 9, 12, 15, 18, 21, 24, 27 or 30 mg) total, taken as lower doses multiple times per day, e.g. 1, 2 3, or 4 times per day, and typically 3 times a day with meals. When taken multiple times per day, the dose may be e.g. from about 1-10 mg (such as about 3, 4, 5, 6, 7, 8, 9, or 10 mg per dose), 3 times per day. Higher doses in the range of e.g. 15-25 mg may be useful for promoting cognition and memory formation in otherwise healthy persons. Alternatively, the typical individual doses may remain the same but the frequency of administration may be decreased e.g. to typically 2 times per day, such as morning and night, or even once per day.

Products comprising the buccal tablets described herein may be provided to a consumer, and include but are not limited to: blister packs comprising a plurality of individual dosage forms or bottles of multiple buccal tablets.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Materials.

Vinpocetine (VPN) was purchased from Wuhan Trustchem Fine Chemical Co., Ltd. Wuhan (Hubei, China). Pullulan was a kind gift from Hayashibara Co., Ltd. (Okayama, Japan). Polyvinyl pyrrolidone (PVP) with an average molecular weight of 24,000 (PVP-K25), 44,000 (PVP-K30), and 360,000 (PVP-K90) were obtained from Spectrum Chemicals & Laboratory Products (New Brunswick, N.J., USA). PVP-VA64, PVP-XL10, PVP-PXL-USP32 were procured from Shanghai Yuking Water Soluble Material Tech Co., Ltd. (Shanghai, China). Aspartame was procured from Sigma-Aldrich (St. Louis, Mo.). Hydroxypropyl methyl cellulose (HPMC) 4000 cp was obtained from Spectrum Chemical Manufacturing Corporation (Gardena, Calif.). Xylitol was procured from Acros organics (Fair Lawn, N.J.). 1-Ethenylpyrrolidin-2-one (PLASDONE™ XL) was provided by ISP (Baar, Switzerland). All chemicals were of analytical grade.

Methods
Preparation of Binary System

VPN polymeric solid dispersions were prepared by either solvent evaporation or lyophilization methods using different PVP grades, namely PVP-K25, PVP-K30, PVP-K90, PVP-VA64, PVP-XL0, and PVP-PXLUSP32 in drug-to-polymer ratios of 1:1, 1:2, and 1:4. Also, mixture of PVP-K25, PVP-K30, and PVP-VA64 in 1:1:1 ratio was prepared and mixed with the drug in 1:4 drug-to-polymer mixture ratio. The specified quantities of the drug and the studied polymer(s) were weighed, dissolved in 10% aqueous acetic acid solution, and shaken well until complete mixing and formation of homogeneously colorless solution that was transferred into a hot air oven at 40° C. until complete evaporation of the solvent and formation of transparent glassy mass. The dried masses obtained were pulverized, passed through sieve no 100, and stored in a desiccator until further evaluation.

For the lyophilization method, drug polymeric solutions were prepared as described above (dissolved in 10% aqueous acetic acid solution, and shaken well until complete mixing and formation of homogeneously colorless solution), transferred to a freezer at −80° C. for 24 hours, and then subjected to freeze-drying for 48 hours using Christ Alpha 1-2 LD Plus lyophilizer (Martin Christ Gefriertrocknungsanlagen GmbH, Osterode am Harz, Germany). Table 1 illustrates the polymers and the drug-to-polymer ratios used to develop solid dispersions by the solvent evaporation and lyophilization methods.

TABLE 1

Aqueous solubility and solubility enhancement of vinpocetine in the prepared solid dispersions.

| Polymer used | Drug: polymer ratio | Vinpocetine solubility (μg/mL) | | Solubility enhancement ratio | |
|---|---|---|---|---|---|
| | | Solvent evaporation | Lyophilization | Solvent evaporation | Lyophilization |
| PVP-K25 | 1:1 | 186.42 | 2014.61 | 80.70 | 872.12 |
| | 1:2 | 340.03 | 2249.39 | 147.19 | 973.76 |
| | 1:4 | 841.35 | 2594.27 | 364.22 | 1123.06 |
| PVP-K30 | 1:1 | 425.58 | 2063.83 | 184.23 | 893.43 |
| | 1:2 | 945.86 | 2312.37 | 409.46 | 1001.02 |
| | 1:4 | 1089.24 | 2567.55 | 471.53 | 1111.49 |
| PVP-K90 | 1:1 | 49.82 | 2102.82 | 21.56 | 910.31 |
| | 1:2 | 91.94 | 2176.18 | 39.80 | 942.07 |
| | 1:4 | 142.34 | 2414.98 | 61.62 | 1045.44 |
| PVP-VA64 | 1:1 | 684.69 | 1708.62 | 296.40 | 739.66 |
| | 1:2 | 1034.39 | 2322.44 | 447.79 | 1005.38 |
| | 1:4 | 1773.26 | 2707.50 | 767.64 | 1172.08 |
| PVP-PXL10 | 1:1 | 31.78 | 1774.59 | 13.75 | 768.22 |
| | 1:2 | 157.75 | 1874.25 | 68.29 | 811.36 |
| | 1:4 | 470.32 | 2020.30 | 203.60 | 874.59 |
| PVP-PXLUSP 32 | 1:1 | 12.62 | 1210.07 | 5.46 | 523.84 |
| | | | | 6.99 | 584.28 |
| | 1:2 | 16.17 | 1349.70 | | |
| | 1:4 | 182.54 | 2047.38 | 79.02 | 886.31 |
| (PVPK25: PVP K30: PVPVA64) (1:1:1) | 1:4 | 1780.99 | 2712.82 | 770.99 | 1174.38 |
| Vinpocetine aqueous solubility | | 2.31 | — | — | |

Abbreviation: PVP, polyvinyl pyrrolidone.

Equilibrium Saturation Solubility

To study the effects of the prepared solid dispersions on the solubility of VPN, the equilibrium solubility was determined as previously reported. (Ahmed et al. Pharm Dev Technol. 2011; 16 (5):497-510). An excess amount of either pure drug or the prepared solid dispersions were added to screw-capped vials containing 10 mL of distilled water. The vials were placed in a thermostatically controlled shaking water bath (Model 1031; GFL Corporation. Burgwedel, Germany) at 25±0.5° C. for 48 h. Samples from the vials were taken and analyzed for VPN concentrations every day until equilibrium was reached; the drug solubility values on two consecutive days did not vary by more than 5%. Aliquots withdrawn were filtered through a 0.22 μm pore-size Millipore filter and assayed for drug content using high performance liquid chromatography (HPLC) method Ding et al. Asian J Pharm Sci. 2015; 10:114-120. doi:10.1016/j.ajps.2014.08.008), with slight modifications. An isocratic HPLC method was performed using Agilent 1200 series equipped with UV diode array detector. A reversed phase C18 analytical column (4×250 mm, 5 μm; Thermo Fischer Scientific) was used. The mobile phase was composed of a mixture of methanol and 0.05 ammonium acetate buffer of pH 5.5, 80:20 (v/v). The flow rate of the mobile phase was 1 mL/min, the injection volume was 20 μL and the detection wave length was 273 nm. Each experiment was performed in triplicate.

Solubilization Efficiency

The solubility of vinpocetine, in the prepared solid dispersions, was compared to the intrinsic drug solubility and the resulting ratios of solubilization efficiency (solubility enhancement) were calculated. These ratios were used to compare the relative solubilization efficiency of VPN in the solid dispersion using both techniques.

Phase Solubility Study and Thermodynamic Parameter of Solubility

An excess amount of pure VPN was added separately into screw-capped vials containing 10 mL of aqueous polyvinyl pyrrolidone vinyl acetate (PVP-VA64) solution (0-10% w/v). The vials were sealed and shaken in a water bath at 37° C. for 72 h. Aliquots (n=3) from each vial were filtered through a 0.22 μm pore-size Millipore filter, and the filtrates were assayed by HPLC. The change in the solubility of VPN resulting from the addition of different PVP-VA-64 concentrations was used to construct a phase-solubility plot and to evaluate the stoichiometry and the stability constant of complexation (Kst), which exemplifies the strength of the interaction and stability of the complex formed.

Calculation of the apparent stability constant, Kst, was achieved from the phase solubility diagram according to the equation described by Higuchi and Connors (Adv Anal Chem Instrum. 1965; 4:117-210), based on the assumption that 1:1 complex was initially formed.

$$Kst = \frac{Slope}{So\,(1 - Slope)} \qquad \text{Higuchi-Connors equation}$$

In the equation, "So" represents the drug solubility in the absence of the studied polymer (the intercept of the phase solubility diagram constructed).

To evaluate the solubilizing efficiency of the studied polymer for the drug, the complexation efficiency ($C_E$) was determined. It was calculated according to the following equation:

$$C_E = So\,K_{1:1} = slope/(1-slope).$$

The Gibbs free energy ($\Delta G°_{tr}$) for the transfer of VPN from pure water to aqueous solutions of PVP-VA-64 was calculated using the following equation:

$$\Delta G°_{tr} = -2.303\,RT\,Log\,(Sc/So)$$

where Sc/So is the ratio of the molar drug solubility in an aqueous solution of PVP-VA-64 to that of pure water. R is the gas rate constant (8.314 J/° C.) and T is the temperature in Kelvin at which the study was conducted. The Gibbs free energy can also be referred to as the thermodynamic potential that is minimized when a system reaches chemical equilibrium from an initial state to a final state at constant pressure and temperature.

Dissolution of the Prepared Solid Dispersion

An in vitro dissolution study of the pure drug and the vinpocetin-PVP-VA64 inclusion complex (equivalent to 5 mg VPN) was performed in triplicate, using the United States Pharmacopeia (USP) dissolution test apparatus II paddle type, DT 700 LH device, Erweka GmbH DT 700 (Heusenstamm, Germany) at 37° C. for 2 h, with a stirring rate of 50 rpm, in 900 mL of enzyme-free simulated intestinal fluid (pH 6.8). Aliquots were collected at 5, 10, 15, 20, 25, 30, 45, 60, 90 and 120 min, with immediate replacement of an equal volume of fluid, and the collected samples were filtered through a 0.22 µm pore-size Millipore filter and assayed for drug content using high performance liquid chromatography (HPLC). From the dissolution profile curve constructed, $DP_{5min}$, $DP_{30min}$ and $DP_{120min}$, the percent of drug dissolved within 5, 30 and 120 minutes, respectively, were estimated. Also, the dissolution efficiency within 10 and 120 minutes, ($DE_{10min}$) and ($DE_{120min}$), respectively and, the mean dissolution time were calculated. For each formulation, the dissolution efficiency was determined as the percent ratio of area under the dissolution profile curve up to the time, t, to that of the area of the rectangle described by 100% dissolution at the same time.

Permeation Study

A buccal permeation study was carried out to determine the feasibility and the impact of administration the drug formulation via this route. In this study, a human oral epithelial cell culture (OEC), Applied Biological Materials Inc., (Richmond, BC, Canada) was used. The cells were cultured, seeded on T25 flasks and the culture medium were replaced every day until the cells were deemed to be suitable for the permeation experiment. This was determined by examination of the electrical resistance and the apparent permeability coefficient. Cells were divided into two groups. Group I was exposed to 0.1 mg/mL VPN in the form of an inclusion complex in dimethyl sulfoxide (DMSO), and group II was subjected to the same concentration of a pure VPN solution in DMSO. Blank cells containing only the culture medium without VPN were used as a reference. Cells (n=3) were incubated, collected after 1, 2, 4, 6 and 24 h, and washed twice with ice-cold phosphate buffered saline. The cell pellets were collected and exposed to two repeated cycles of freezing and thawing, and finally to ultrasonication for 10 min for complete rupture of the cells. Cell lysates were subjected to centrifugation using a 3K30 sigma laboratory centrifuge (Ostrode am Harz, Germany) at 15,000×g for 1 h at 4° C. The concentration of VPN in the supernatant was determined using HPLC. VPN standards containing known amounts of the drug in the studied cells were prepared, treated as described above and analyzed before estimation of the unknown drug concentrations in the samples.

Physicochemical Characterization of VPN in the Solid Dispersion Mixture

Differential Scanning Calorimetry (DSC)

The thermal behavior of VPN, PVP-PVA64, and the lyophilized solid dispersion were studied using a Shimadzu differential scanning calorimetry TA-50 ESI DSC apparatus (Tokyo, Japan) calibrated with indium. Analysis of all the studied samples was performed from 10 to 300° C. with a 10° C./min heating rate.

Fourier Transform Infrared (FT-IR) Spectroscopy

Spectra of samples used in the DSC study were collected using Nicolet iS10 (Thermo Scientific, Inc., Waltham, Mass.) at a resolution of 4 $cm^{-1}$, and the number of scans was 36. Frequency was in the range of 4000-500 $cm^{-1}$.

X-Ray Powder Diffraction (XRPD)

Changes in the crystalline state of the prepared VPN-PVP-VA64 solid dispersion compared to that of pure VPN powder were studied using a powder X-ray diffractometer (D/max 2500, Rigaku, Tokyo, Japan). The diffraction patterns of the pure drug and solid dispersion were recorded at a scan speed of 0.5000 degree/min.

Formulation of Lyoplant-Tabs

Experimental Design

A three-level factorial design was used to study the effect of the concentration of the aqueous pullulan solution (X1) and the concentration of the wetting-aid polymer, PLAS-DONE™ XL (X2) on the cumulative drug released (Y1) and the wetting index (Y2) of the lyoplant-tabs utilizing StatGraphics Centurion XV version 15.2.05 software (StatPoint Technologies, Inc., Warrenton, Va., USA). Concentrations of 5-15% and 4-6% were used for X1 and X2, respectively. The study was conducted to maximize Y1 and Y2. Table 2 shows the compositions of the formulations.

TABLE 2

Composition of the lyoplant-tabs formulations along with the observed, fitted values and statistical analysis of variance (ANOVA) of the studied responses Y1 and Y2

| Run | X1 (%) | X2 (%) | Y1 (%) Observed | Y1 (%) Fitted | Y2 (%) Observed | Y2 (%) Fitted |
|---|---|---|---|---|---|---|
| 1 | 15 | 5 | 67.68 ± 2.63 | 65.58 | 67.72 ± 5.68 | 72.40 |
| 2 | 5 | 4 | 76.64 ± 1.99 | 76.89 | 92.67 ± 2.17 | 101.48 |
| 3 | 10 | 6 | 92.24 ± 7.98 | 91.35 | 90.04 ± 7.38 | 96.94 |
| 4 | 10 | 4 | 77.97 ± 3.99 | 76.53 | 77.08 ± 8.29 | 66.15 |
| 5 | 15 | 4 | 67.35 ± 4.49 | 68.54 | 57.85 ± 7.34 | 59.97 |
| 6 | 5 | 5 | 80.96 ± 5.99 | 80.73 | 134.26 ± 7.77 | 125.56 |
| 7 | 15 | 6 | 75.65 ± 3.58 | 76.56 | 85.90 ± 10.73 | 79.10 |
| 8 | 5 | 6 | 98.54 ± 2.63 | 98.51 | 144.03 ± 12.5 | 143.92 |
| 9 | 10 | 5 | 74.65 ± 1.72 | 76.97 | 80.39 ± 8.17 | 84.41 |

TABLE 2-continued

Composition of the lyoplant-tabs formulations along with the observed, fitted values and statistical analysis of variance (ANOVA) of the studied responses Y1 and Y2

| | Analysis of Variance (ANOVA) | | | | | |
|---|---|---|---|---|---|---|
| | Y1 | | | Y2 | | |
| Factors | Estimated Effect | F-ratio | P-value | Estimated Effect | F-ratio | P-value |
| X1 | −15.15 | 68.80 | 0.0037 | -53.1633 | 31.10 | 0.0114 |
| X2 | 14.82 | 65.84 | 0.0039 | 30.79 | 10.43 | 0.0482 |
| X1X1 | −7.63 | 5.82 | 0.0948 | 29.1367 | 3.11 | 0.1758 |
| X1X2 | −6.80 | 9.24 | 0.0559 | −11.655 | 1.00 | 0.3918 |
| X2X2 | 13.94 | 19.40 | 0.0217 | −5.72333 | 0.12 | 0.7518 |
| $R^2$ | 98.26% | | | 93.85% | | |
| Adj. $R^2$ | 95.35% | | | 83.59% | | |

Abbreviations: X1, Aqueous pullulan solution; X2, PLASDONE ™ XL; Y1, Cumulative drug release; Y2, wetting index.

Preparation of the Lyoplant-Tabs

Buccal freeze-dried pullulan-based tablets (lyoplant-tabs) were prepared according to the method previously described for development of Vitamin K and finasteride lyophilized tablets (Ahmed et al. *Drug Dev Ind Pharm.* 2018; 44(4): 652-661. doi: 10.1080/03639045.2017.1405977; El-Say et al. *J Pharm Sci.* 2017; 106:2447-2456. doi:10.1016/j.xphs.2017.01.001). Briefly, three different pullulan solutions (5, 10 and 15° %) were prepared by dissolving the specified quantity of pullulan in distilled water over a magnetic stirrer. A quantity of the lyophilized binary system equivalent to 100 mg VPN, HPMC (2% w/v), aspartame (0.125% w/v), xylitol (1.6% w/v) and PLASDONE™ XL (4-6% w/v) were homogenously dispersed in 10 mL of the specified pullulan solution. A weight equivalent to 5 mg VPN of the prepared mixture was carefully poured into an empty pocket of a tablet blister pack that were then frozen at −80° C. for 24 h and then subjected to freeze drying for 48 h using a Christ Alpha 1-2 LD Plus lyophilizer (Martin Christ Gefrier-trocknungsanlagen GmbH, Osterode am Harz, Germany). The obtained freeze-dried tablets were kept at 25° C. in a desiccator containing calcium chloride until further study.

Evaluation of the Prepared Tablets

All the prepared tablets were characterized for weight variation, thickness, drug content, friability, wetting time, wetting index, and in-vitro drug release based on the specifications mentioned in USP 28/NF23 (The United States Pharmacopeia TNF. UISP 28/NF 23. Rockville, Md., USA: US Pharmacopoeial Convention Inc.; 2005). Ten tablets from each run were weighed individually using a Mettler Toledo AJ100, electric balance (Greifensee, Switzerland) and the average weight was calculated. Tablet thickness was estimated using a Mitutoyo dial thickness gauge (Kawasaki, Japan) for the same number of tablets. For determination of the drug content, six tablets from each run were randomly selected and placed separately in screw cap glass bottles containing 100 mL of 10% acetic acid solution. The mixtures were thoroughly mixed in a thermostatically controlled shaking water bath at 25° C. for 24 h, then homogenized using an UltraTurax, IKA® T18 basic Homogenizer (Campinas, Brazil). The content of the bottles was subsequently filtered using Acrodisc® syringe filters of 0.45 mm. The drug concentration in the filtrate was determined using the HPLC method described above.

Friability of the prepared tablets was assessed using Erweka Friabilator type PTF1, Pharma-test (Hainburg, Germany). Ten tablets from each run were de-dusted, weighed, and allowed to rotate for 4 minutes at 25 rpm; after which the tablets were de-dusted and weighed again. Friability was expressed as the loss of weight and calculated as a fraction of the original tablets weight using the following equation:

$$\text{Tablet friability (\%)} = \left[\frac{(\text{Original weight} - \text{Final weight})}{\text{Original weight}}\right] \times 100$$

Wetting time and the wetting index of the tablets were evaluated by weighing three individual tablets from each run and placing each tablet in the center of a petri dish containing a tissue paper that was folded twice and kept wetted with a small volume (8 mL) of rhodamine dye solution. The time taken until first appearance of the dye on the tablet surface was taken as the wetting time. The wetting index was estimated by reweighing the wetted tablet, then applying the following equation:

$$\text{Swelling Index (\%)} = \frac{\text{Weight of the wetted tablet} - \text{Tablet initial weight}}{\text{Tablet initial weight}} \times 100$$

In-Vitro Drug Release Study

The release of VPN from the lyoplant-tabs formulations was carried out using USP dissolution test apparatus type II (Paddle type), DT 700 LH device, Erweka GmbH DT 700 (Heusenstamm, Germany). The study was conducted in 900 mL phosphate buffer of pH 6.8 at 37° C. Paddles were rotated at 50 rpm and aliquots of 3 mL were withdrawn, with immediate replacement, for 120 minutes and analyzed for VPN content using the HPLC method described earlier. The results obtained were the average of three measurements. The conditions of the experiment were selected to achieve sink conditions.

Experimental Design Statistical Analysis

Data obtained for Y1 and Y2 were statistically analyzed (p-value <0.05) to determine the significant factors that affected each studied response. This was achieved by introducing the obtained results into the response column of the StatGraphics software, after which the model was run.

Preparation and Characterization of the Optimized Tablets

The proposed optimized tablet formulation was prepared and characterized for the same quality attributes that have been previously described, and the data obtained for cumulative drug release and swelling index were compared to the predicted values.

Evaluation of the Clinical Pharmacokinetic Behavior

The pharmacokinetic parameters and the plasma concentration time curve for VPN in the optimized lyoplant-tabs formulation, pure drug lyophilized buccal tablets and commercial oral drug tablets were studied following administration to healthy volunteers. Pure VPN buccal tablets were prepared as previously described except that pure VPN was used instead of the drug binary system.

The health status of nine male Egyptian volunteers, aged from 21 to 30 years old with a body mass index of 20-30 kg/m$^2$, was confirmed after considering their medical history and carrying out physical examinations and laboratory investigations. Subjects participating in the study were asked to read, understand, and sign a written consent about the nature of the research. Before administration of the formulations, volunteers were kept in-house and were not allowed to get any medication for two days. Subsequently, blood samples were withdrawn at pre-determined periods for 24 h. The study was performed in accordance with European Medicines Agency (EMA), International Conference on Harmonization (ICH), Good Clinical Practice (GCP), Food and Drug Administration (FDA) guidelines and the Declaration of Helsinki. The Protocol was approved by the Ethics Committee of the Egyptian Research and Development Company (ERDC).

A single-dose one-period parallel design was conducted. Volunteers were classified into three groups (n=3); group I (test group) was given the optimized lyoplant-tabs formulation, group II (positive control group) was administered the buccal tablets containing pure drug, while group III (reference group) was given the commercial VPN tablets namely; VINPORAL® 5 mg (Amriya Pharmaceutical Industries Company, Alexandria, Egypt). Volunteers of group I and II were asked to hold the tablets in the cheek. Venus blood samples of 5 mL were collected from every volunteer for 24 h and the concentration of VPN in the collected samples was determined as described below.

Chromatographic Conditions

A high-performance liquid chromatographic method coupled with MS/MS detection (HPLC-MS/MS) was developed, optimized and validated at the ERDC laboratories for the determination of VPN in human plasma. An Agilent HPLC series 1200, Agilent Technologies, Deutschland GmbH (Waldbronn, Germany) equipped with G1311A quaternary pump, G1329A autosampler, G1322A vacuum degasser and mass hunter software was used. The mobile phase consisted of 75% acetonitrile: 25% (10 mM ammonium acetate and 50 pIL formic acid for each 100 ml water). It was pumped at a flow rate of 0.30 mL/min and a reverse phase column Intersil ODS-3 (4.6 mm×50 cm, dp 5 μm Sigma-Aldrich) equilibrated at 25° C. Retention times of 1.74 and 3.47 minutes were detected for galantamine (internal standard) and VPN, respectively. The method was fully validated according to the "FDA Bio-analytical Method Validation Guidelines 2003". Linearity of the assay method was verified within the concentration range of 0.125-25 ng/mL with a regression coefficient ($R^2$)=0.9983. All the results were within the acceptance criteria as stated in the recommended guidelines. The mean recovery of VPN was 103.2 at 0.125 ng/mL (low limit of quantification) and 94.4% at 25 ng/mL (upper limit of quantification).

Plasma Calibration Curve and Sample Collection

VPN and IS stock methanolic solutions were prepared by dissolving an accurately weighed amount of each drug in a separate volumetric flask. Calibration standards in blank human heparinized plasma were freshly prepared in duplicate at final VPN plasma concentrations of 0.125, 0.250, 0.5, 0.750, 1.5, 2.5, 5, 7.5, 10, 15, 20 and 25 ng/mL for every analytical run. A fixed volume of 50 pIL IS (4 μg/mL) was added for each VPN sample. Quality control (QC) samples were prepared independently from the calibration standards, using separately prepared master stock solutions. These solutions were diluted with control human plasma to produce the following QC samples: LLOQ 0.125 ng, QC low (QCL) 0.375 ng, QC mid (QCM) 12.5 ng and QC high (QCH) 22.5 ng.

Pharmacokinetic Data Analysis

A non-compartmental pharmacokinetic model using KINETICA™ pharmacokinetic software (version 4; Thermo Fisher Scientific, Inc.) was utilized to determine the following pharmacokinetic parameters. Maximum plasma concentration over the time span ($C_{max}$), time point of maximum plasma concentration ($T_{max}$), the apparent first-order absorption rate constant ($K_{abs}$), the absorption half-life ($t_{1/2\ abs}$), the apparent first-order elimination rate constant ($K_{elm}$), the elimination half-life ($t_{1/2\ elm}$), apparent volume of distribution (Vd), total clearance rate (TCR), area under the plasma concentration-time curve from time zero to the last measurable drug concentration ($AUC_{0-last}$), area under the moment curve ($AUMC_{0-last}$) and mean residence time (MRT). The data obtained were expressed as mean±SD and statistically analyzed using GraphPad Prism 6 (GraphPad Software, San Diego, Calif.). To indicate the significant difference between the optimized lyoplant-tabs, the drug commercial oral tablet and pure drug loaded buccal lyophilized tablets, 2-way ANOVA followed by Tukey's multiple comparisons test was used. P-value <0.05 was considered to be statistically significant.

Results and Discussion

Equilibrium Saturation Solubility and Solubilization Efficiency

The solubility of VPN in water at 25° C. was found to be 2.31 pig/mL. Accordingly, VPN is considered a practically water insoluble drug. Different PVP grades were used as hydrophilic carriers to enhance the drug aqueous solubility. Solvent evaporation and lyophilization were the techniques employed to prepare drug binary systems. Results of the equilibrium solubility and solubility enhancement ratio revealed that lyophilization was superior to the solvent evaporation technique and the drug binary system with PVP-VA64 in a 1:4 ratio was the best among all the studied carriers, as illustrated in Table 1.

Three drug to polymer ratios were studied to evaluate the effect of increasing the polymer concentration on drug solubility. Results indicated that drug solubility was augmented as the concentration of the polymer was increased, an effect which could be attributed to uniform distribution of VPN on the polymer surface. Further description of this behavior is provided below in the discussion of the type of complexation in the phase solubility study section.

In this study, PVP-VA 64 was superior to all the studied carriers in enhancing the solubility and solubilization efficiency of VPN following development of the binary system by either the solvent evaporation or the lyophilization method (Table 1).

Phase Solubility Study and Thermodynamic Parameter of Solubility

To study the interaction of VPN with PVP-VA-64, phase solubility was studied, and the diagram obtained is represented in FIG. 1A. It was clear that the drug solubility was increased upon increasing the polymer concentration. The following chart equation was obtained:

$$Y=0.0014X+0.0002$$

The values of the stability constant Kst and the complexation efficiency $C_E$ were found to be 7 mL$^{-1}$ mg, 0.0014 respectively. These results are in good agreement with and accordance with the well-established formation of drug soluble complexes between water soluble polymeric carriers such as PVP-VA-64 and poor water soluble drugs such as VPN.

Carrier drug complexes have been classified according to the effect of the carrier on the drug solubility. Type-A is obtained when the drug solubility is increased upon increasing the polymer concentration. When this complex is first order with respect to the carrier and first or higher order with respect to the drug then AL-type is obtained. If the obtained complex is first order with respect to the drug, but second or higher order with respect to the carrier then AP-type is obtained. B-type complexes are obtained when there is a limited solubility of the drug in the aqueous complexation medium, i.e., increase solubility of the drug with the increase of the polymer concentration up to a certain limit followed by plateau. In this study, upon construction of VPN phase solubility profile, FIG. 1A, AP-type complexation was obtained.

The values for $\Delta G°_{tr}$ give information about the process of drug solubilization whether it is favorable or not. Negative values for $\Delta G°_{tr}$ indicate favorable conditions and the lower the negative values obtained the more promising the condition. Results for VPN $\Delta G®_{tr}$ for 1, 2, 3, 4, 5, 6, 7, 8, 9 and 10% polymeric solution were −4789.515, −6330.538, −7390.998, −8413.708, −8775.631, −9159.485, −9686.917, −10097.66, −10278.36 and −10658.79 J/mol, respectively. All the obtained values were negative and decreased as the polymeric solution increased. This indicated increased solubility of VPN in the presence of PVP-VA-64 and demonstrated the spontaneous solubilization tendency of the drug in the polymeric solution, which become more satisfactory when the concentration of the polymer increased.

Dissolution of the Prepared Solid Dispersion

The in vitro dissolution of pure VPN and the prepared drug PVP-VA-64 binary system is demonstrated in FIG. 1B. Data obtained from the dissolution profile curve were used to estimate $DP_{5min}$, $DP_{30min}$ and $DP_{120min}$ in which the obtained values were 5.62±2.45%, 16.46±3.58% and 22.41±6.04% for the pure drug, and 31.09±3.92%, 62.52±5.34% and 74.61±3.19% for the binary system, respectively. Also, $DE_{10min}$ was calculated and found to be 2.17±0.23% and 0.428±0.159% for the complex and the pure drug, respectively. The $DE_{120}$ for the complex and the pure drug were 65.35±2.5% and 18.67±3.73%, respectively.

From the results obtained, it is evident that the binary system considerably enhanced the in vitro dissolution when compared to pure drug. In general, this behavior could be attributed to improved drug solubility through conversion of VPN from the crystalline to the amorphous state, reduction of drug crystal size and the absence of aggregation of drug crystals. The dissolution rate of VPN from the binary system was found to be higher than that of the corresponding pure drug, (FIG. 1B), owing to better wettability and prevention of particle aggregation.

Permeation Across the Buccal Mucosa

The ability of VPN to permeate through the oral buccal mucosal cells was evaluated. VPN in the form of binary system with PVP-VA-64 and pure drug were used. Effective permeation of VPN from the human oral epithelial cell culture, OEC, is expected to have a positive impact in the drug bioavailability and the therapeutic response.

Results of the permeation study revealed that drug binary system enhanced the rate but not the extent of drug permeation (data not shown). This finding indicates that complexation does not alter but accelerates the process of drug transport across the OEC. Previous reports illustrated that VPN is well absorbed from the gastrointestinal tract particularly from the small intestine. In this study, the transport of VPN, in the form of both pure VPN solution and binary system, was also possible from the oral epithelial cells, with a preference for the binary system due to the fast rate of drug permeation and suitability of the binary system for buccal tablet formulation.

Physicochemical Characterization

Figure 2:
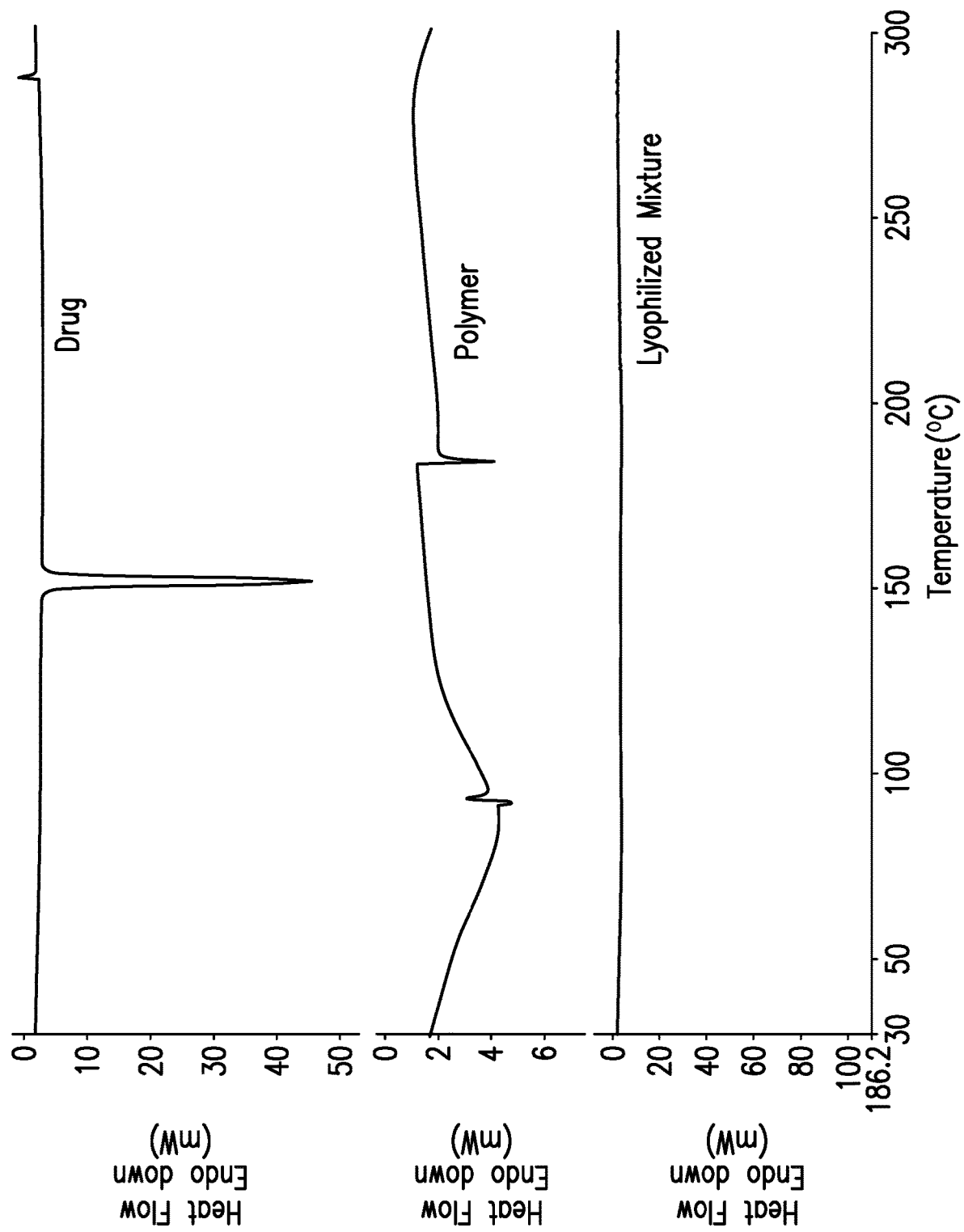
FIG. 2. Differential scanning calorimetry thermograms of vinpocetine, polyvinyl pyrrolidone vinyl acetate, and lyophilized binary mixture.

The thermal behavior of pure VPN exhibited a sharp endothermic peak at 152.28° C., typically of a crystalline anhydrous drug structure as previously reported (FIG. 2). An endothermic peak was observed in the polymer thermogram at the range 80-100° C. which is attributed to water loss from the hygroscopic polymer upon heating. Another peak corresponding to the polymer glass transition temperature was also detected at 186° C. The prepared solid dispersion showed no crystalline peak of VPN which implies that the drug is present in completely amorphous form and is molecularly dispersed in the polymeric matrix. The DSC spectra of the prepared VPN solid dispersion also indicated no chemical interaction since no new peaks for any new chemical moiety was observed.

Figure 3:
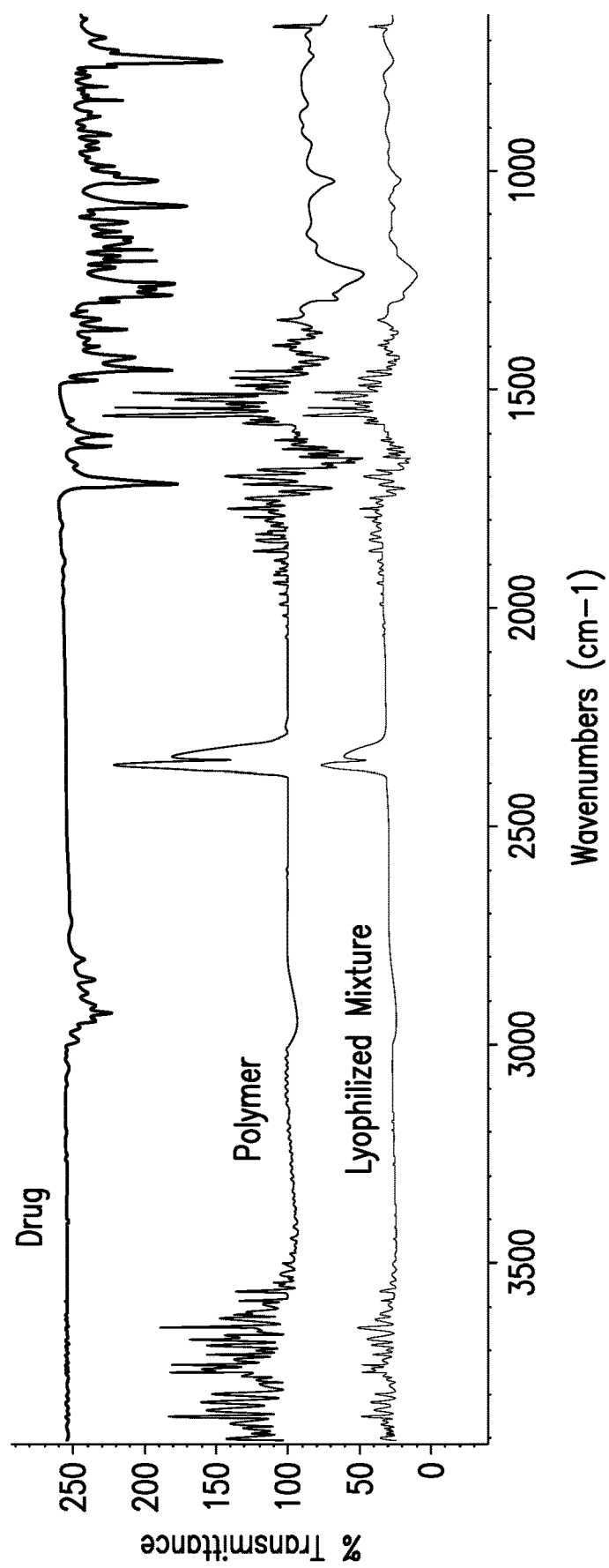
FIG. 3. Fourier transform infrared spectra of vinpocetine, polyvinyl pyrrolidone vinyl acetate, and lyophilized binary mixture.

The FTIR spectrum of VPN, depicted in FIG. 3, showed a characteristic sharp peak at 1720 cm$^{-1}$ equivalent to carbonyl stretching. Another distinct absorption band was detected in the region 2840-3000 cm$^{-1}$ which is assigned to aromatic stretching. No new peaks or substantial shifting in the position of the drug or PVP functional groups were observed in the developed solid dispersion except for some overlapping between both, VPN and PVP, at specified positions owing to presence of common functional groups.

Figure 4A:
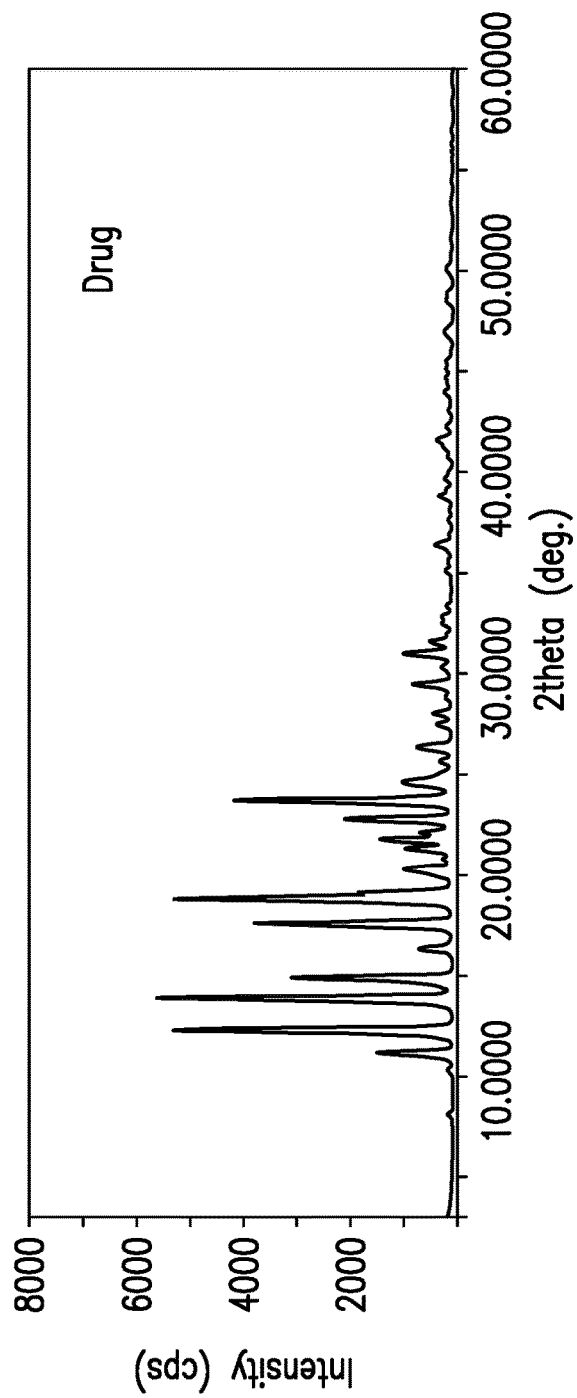
FIGS. 4A and B. X-ray powder diffraction patterns of pure vinpocetine (A) and the lyophilized binary mixture (B).
Figure 4B:
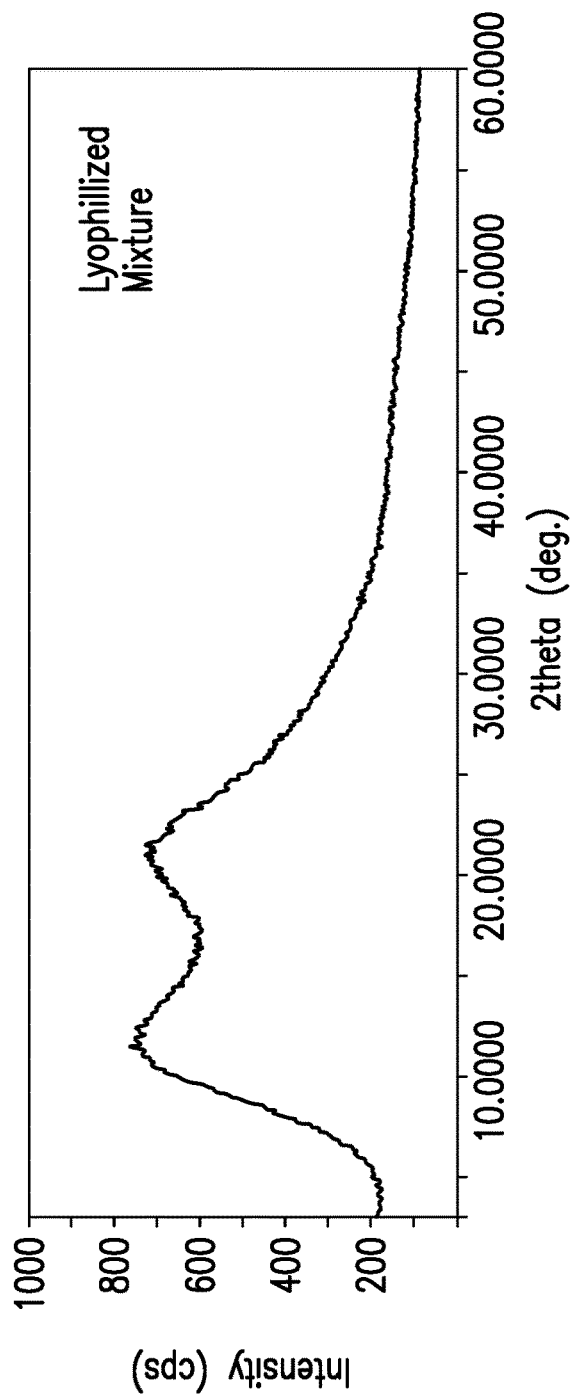

The X-ray diffraction pattern of pure VPN showed distinct characteristic peaks of the crystalline drug structure as illustrated in FIG. 4, while XRPD of the solid dispersion was different from that of the pure drug, which is an indication of the crystalline state transformation into the amorphous form. This transformation may result in enhancement in the aqueous drug solubility.

Lyoplant-Tabs Formulation Development

Lyoplant-tabs were prepared utilizing pullulan, hydroxypropyl methylcellulose (HPMC), aspartame, xylitol and PLASDONE™ XL. HPMC was used as a binder, and also it acts as a mucoadhesive polymer since buccal dosage forms are supposed to exhibit sufficient adhesion to the mucosa and resist the salivation and mechanical movements in the mouth for a sufficient period of time. Aspartame (0.125%) was added as a sweetener while xylitol (1.6%) was incorporated to enhance the quality attributes of the prepared tablets since it has more negative heat of solution and lesser hygroscopicity when compared to mannitol and sorbitol, which are commonly used in pharmaceutical formulations designed to disintegrate in the oral cavity. PLASDONE™ XL was used to facilitate swelling of the prepared tablets (swelling-aid polymer). Faster water diffusion and wetting have been reported to enhance the formation of adhesive bonds (rapid adhesion) and so mucoadhesion in buccal tablets. Pullulan, a naturally derived polysaccharide polymer, possesses unique characteristics that make it ideal for pharmaceutical dosage forms. It is very stable and matches the performance properties of gelatin. In this work, we studied the effect of pullulan and wetting-aid polymer concentrations to develop buccal pullulan-based tablets utilizing the lyophilization technique.

Characterization of Lyoplant-Tabs

The studied characteristics of the prepared lyoplant-tabs are represented in Tables 3a and 3b. Weight and thickness were in the range of 108.05±1.94-167.03±6.07 mg and 3.93±0.20-4.91±0.42 mm, respectively. Friability ranged from 0.046-0.560% which is less than 1%. Wetting time was in the range 4.33±0.22-14.51±1.57 minutes, while results of the drug content showed an average value of 98.04±0.34-102.9±0.21%. All the studied characteristics are in good agreement and met the USP specifications.

TABLE 3a

Quality attributes of the prepared pullulan-tabs formulations

| Run | Weight (mg) | Thickness (mm) | Friability (%) | Wetting time (minutes) | Drug content (%) |
|---|---|---|---|---|---|
| 1 | 162.38 ± 3.11 | 4.32 ± 0.12 | 0.560 | 14.06 ± 0.21 | 98.04 ± 0.34 |
| 2 | 108.05 ± 1.94 | 4.02 ± 0.13 | 0.143 | 4.69 ± 0.13 | 99.34 ± 0.11 |
| 3 | 138.77 ± 3.50 | 4.28 ± 0.09 | 0.417 | 6.04 ± 1.00 | 101.03 ± 0.28 |
| 4 | 133.92 ± 5.36 | 4.15 ± 0.18 | 0.098 | 7.53 ± 0.42 | 102.4 ± 0.05 |
| 5 | 162.29 ± 1.82 | 4.62 ± 0.15 | 0.095 | 14.51 ± 1.57 | 102.9 ± 0.21 |
| 6 | 114.62 ± 2.52 | 4.13 ± 0.13 | 0.139 | 4.43 ± 0.21 | 98.60 ± 0.41 |
| 7 | 167.03 ± 6.07 | 4.91 ± 0.42 | 0.046 | 8.75 ± 0.46 | 99.62 ± 0.17 |
| 8 | 116.88 ± 4.96 | 3.93 ± 0.20 | 0.066 | 4.33 ± 0.22 | 98.06 ± 0.33 |
| 9 | 134.28 ± 4.17 | 4.20 ± 0.19 | 0.232 | 8.83 ± 0.80 | 100.61 ± 0.05 |

Effect of the studied variables on Y1 and Y2

Results for the cumulative drug release and wetting index were statistically analyzed using multiple regression analysis and two-way ANOVA utilizing the StatGraphics software. Table 3b illustrates the values for estimated effects, F-ratios and P-values obtained. Positive values for estimated effect is an indication of a synergistic effect for the studied variable on this response and vice versa. To compare the actual and expected variations in the variable averages F-ratio is used, in which an F-ratio that is greater than 1 is a sign of a location effect and hence P-value is used to indicate the significant effect if its value differs from 0 and is less than 0.05.

TABLE 3b

Composition of the lyoplant-tab formulations along with the observed, fitted values and statistical ANOVA of the studied responses Y1 and Y2

| Run | X1 (%) | X2 (%) | Y1 (%) Observed | Fitted | Y2 (%) Observed | Fitted |
|---|---|---|---|---|---|---|
| 1 | 15 | 5 | 67.68 ± 2.63 | 65.58 | 67.72 ± 5.68 | 72.40 |
| 2 | 5 | 4 | 76.64 ± 1.99 | 76.89 | 92.67 ± 2.17 | 101.48 |
| 3 | 10 | 6 | 92.24 ± 7.98 | 91.35 | 90.04 ± 7.38 | 96.94 |
| 4 | 10 | 4 | 77.97 ± 3.99 | 76.53 | 77.08 ± 8.29 | 66.15 |
| 5 | 15 | 4 | 67.35 ± 4.49 | 68.54 | 57.85 ± 7.34 | 59.97 |
| 6 | 5 | 5 | 80.96 ± 5.99 | 80.73 | 134.26 ± 7.77 | 125.56 |
| 7 | 15 | 6 | 75.65 ± 3.58 | 76.56 | 85.90 ± 10.73 | 79.10 |
| 8 | 5 | 6 | 98.54 ± 2.63 | 98.51 | 144.03 ± 12.5 | 143.92 |
| 9 | 10 | 5 | 74.65 ± 1.72 | 76.97 | 80.39 ± 8.17 | 84.41 |

TABLE 3b-continued

ANOVA

| Factors | Y1 Estimated effect | F-ratio | P-value | Y2 Estimated effect | F-ratio | P-value |
|---|---|---|---|---|---|---|
| X1 | −15.15 | 68.80 | 0.0037 | −53.1633 | 31.10 | 0.0114 |
| X2 | 14.82 | 65.84 | 0.0039 | 30.79 | 10.43 | 0.0482 |
| X1X1 | −7.63 | 5.82 | 0.0948 | 29.1367 | 3.11 | 0.1758 |
| X1X2 | −6.80 | 9.24 | 0.0559 | −11.655 | 1.00 | 0.3918 |
| X2X2 | 13.94 | 19.40 | 0.0217 | −5.72333 | 0.12 | 0.7518 |
| R2 | 98.26% | | | 93.85% | | |
| Adj. R2 | 95.35% | | | 83.59% | | |

Abbreviations: X1, aqueous pullulan solution; X2, plasdone XL; Y1, cumulative drug release; Y2, wetting index The equations obtained of the fit model were:

$$Y1 = 180.011 + 4.938X1 - 55.472X2 - 0.153X1^2 - 0.680X1X2 + 6.968X2^2$$

$$Y2 = -10.944 - 11.144X1 + 55.667X2 + 0.583X1^2 - 1.166X1X2 - 2.862X2^2$$

The observed values for Y1 and Y2 were in the range of 67.35±4.49-98.54±2.63% and 57.85±7.34-144.03±12.5%, respectively as shown in Table 3b. Aqueous pullulan solution concentration (X1), the concentration of the wetting-aid polymer; PLASDONE™ XL (X2) and the quadratic effect of X2 were significantly affecting Y1 at P-values of 0.0037, 0.0039 and 0.0217, respectively, while X1 and X2 were significantly affecting Y2 at P-values of 0.0114 and 0.0482, respectively. Pareto charts obtained, which are depicted in FIG. 5, also confirmed the above finding. A vertical reference line at P-value of 0.05 is denoted in the chart in which an effect that exceeds this reference line is statistically significant. The X1 was negatively (antagonistically) affecting both Y1 and Y2 while, X2 was positively (synergistically) affecting the same responses.

As the pullulan concentration was increased the cumulative drug release and the swelling index were decreased owing to the formation of a water swollen gel like structure that prevent the penetration of the dissolution medium or rhodamine dye solution into the matrix. The concentration of the wetting-aid polymer was found to be critical. PLASDONE™ XL possesses hygroscopic, or water-attracting characteristics with excellent swelling properties that promotes water absorption, rapid water uptake and so wetting of the tablet due to formation of porous structure. The effect of changing the concentrations of X1 and X2 on Y1 and Y2 is illustrated in the estimated response surfaces (FIG. 5).

To develop an optimized lyoplant-tab characterized by a maximized cumulative drug release and swelling index over the indicated region, the optimum desirability that accomplishes this goal was identified. The suggested values for X1 and X2 were found to be 5 and 6%, respectively and the predicted values for Y1 and Y2 were calculated to be 98.51 and 143.92%, respectively. The observed values were close to the predicted ones with standard errors not greater that 5%.

Clinical Pharmacokinetic Study

Figure 6:
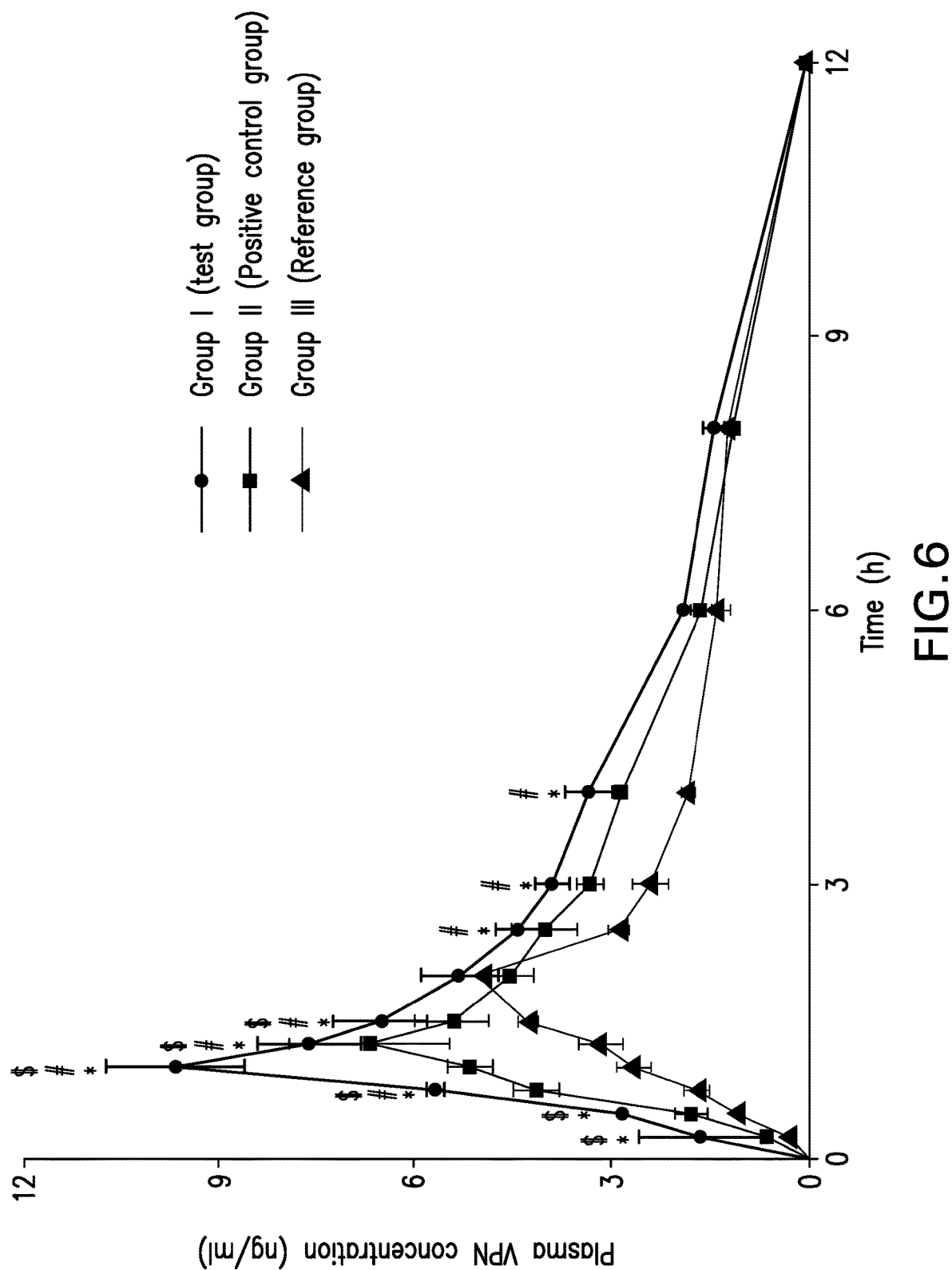
FIG. 6. Plasma concentration-time curves for VPN after oral administration of commercial drug product and buccal formulation to human volunteers. Note: $^{\$}$ indicates significant difference (p<0.05) between group I and II, * indicates significant difference (p<0.05) between group I and III, while $^{\#}$ indicates significant difference (p<0.05) between group II and III.

Plasma concentration-time curves of VPN following administration of a single dose of 5 mg VPN in the form of oral commercial drug tablets, and lyophilized drug buccal tablets are shown in FIG. 6. Maximum VPN plasma concentrations of 9.658±1.074, 6.672±1.234 and 5.050±0.239 ng/mL were observed after 1, 1.25 and 2.5 h for the optimized lyoplant-tabs, buccal lyophilized tablets containing pure drug and commercial VPN tablets, respectively.

These finding confirmed the advantage of the lyoplant-tabs formulation in the rate and extent of VPN absorption. Other studied pharmacokinetic parameters are depicted in Table 5. Lyoplant-tabs demonstrated higher AUC and AUMC compared to the other formulations. Moreover, lyoplant-tab showed relative bioavailability of 123.37 and 159.64% with the buccal lyophilized tablets containing pure drug and commercial VPN tablets, respectively. Overall, enhanced pharmacokinetic parameters and drug bioavailability were observed with the group administered the optimized lyoplant-tabs formulation which indicate that enhancement of the VPN aqueous solubility by complexation with PVP-VA-64 using the lyophilization technique and administration of the drug binary system through the buccal route following development of pullulan based solid dosage form utilizing the lyophilization technique could be considered as a promising formulation and an excellent alternative for the currently available VPN marketed product.

TABLE 5

Pharmacokinetic parameters of the oral commercial and buccal vinpocetine tablets

| Pharmacokinetic parameter | Group I (Test group) | Group II (Positive control group) | Group III (Reference group) |
| --- | --- | --- | --- |
| $C_{max}$ (ng/mL) | 9.658 ± 1.074 | 6.672 ± 1.234 | 5.050 ± 0.239 |
| $T_{max}$ (h) | 1.000 ± 0.000 | 1.250 ± 0.000 | 2.500 ± 0.000 |
| $K_{abs}$ (h$^{-1}$) | 1.404 ± 0.020 | 1.165 ± 0.102 | 0.806 ± 0.019 |
| $t_{(1/2)\ abs}$ (h) | 0.494 ± 0.007 | 0.596 ± 0.051 | 0.860 ± 0.021 |
| $K_{elm}$(h$^{-1}$) | 0.444 ± 0.039 | 0.406 ± 0.104 | 0.565 ± 0.001 |
| $t_{(1/2)\ elm}$ (h) | 1.569 ± 0.138 | 1.774 ± 0.396 | 1.227 ± 0.001 |
| Vd (L) | 0.456 ± 0.026 | 0.624 ± 0.071 | 0.655 ± 0.015 |
| TCR (mL/min.) | 3.364 ± 0.210 | 4.157 ± 0.517 | 6.163 ± 0.151 |
| $AUC_{0\text{-}last}$ (ng · h/mL) | 30.319 ± 1.691 | 24.575 ± 0.278 | 18.992 ± 0.729 |
| $AUMC^{0\text{-}last}$ (ng · h$^2$/mL) | 108.024 ± 6.355 | 90.946 ± 1.696 | 76.703 ± 3.551 |
| MRT (h) | 3.563 ± 0.040 | 3.701 ± 0.059 | 4.038 ± 0.032 |

$C_{max}$, maximum plasma concentration; $T_{max}$, time point of maximum plasma concentration; $K_{abs}$, the apparent first-order absorption rate constant; $t_{1/2\ abs}$, the absorption half-life; $K_{elm}$, the apparent first-order elimination rate constant; $t_{1/2\ elm}$, the elimination half-life; Vd, apparent volume of distribution; TCR, total clearance rate; $AUC_{0\text{-}last}$, area under the plasma concentration-time curve from time zero to the last measurable drug concentration; $AUMC_{0\text{-}last}$, area under the moment curve; MRT, mean residence time.

SUMMARY

As discussed above, different hydrophilic carriers have been examined and their effect on the preparation of VPN solid dispersions in order to enhance the drug's aqueous solubility has been demonstrated. The drug/PVP-VA-64 binary system developed using a lyophilization technique was superior when compared with the other studied carriers. Similar results would accrue with other drugs or drug systems. The drug to polymer ratio significantly affected the solubility of the drug from the prepared solid dispersion systems. Physicochemical characterization confirmed the presence of the drug in completely amorphous form and it was molecularly dispersed in the polymeric matrix. The concentrations of pullulan and the wetting-aid polymer (PLASDONE™ XL) significantly affected the development of the buccal pullulan-based tablets. Variations on the selection of the wetting aid and other parameters can be practiced within the scope of the present invention. The lyophilization technique that was utilized to develop an optimized lyoplant-tablet was successfully implemented to develop solid dosage form with acceptable quality attributes. The technique augmented the bioavailability of vinpocetine, a drug characterized by poor aqueous solubility and limited bioavailability, especially when a binary system of vinpocetine was used.

We claim:

1. A pharmaceutical composition in a buccal solid dosage form comprising,
   vinpocetine,
   polyvinyl pyrrolidone, and
   at least one excipient
   wherein,
   the ratio vinpocetine:polyvinyl pyrrolidone is from: 1:1 to 1:4, and
   the vinpocetine and the polyvinyl pyrrolidone are lyophilized to form a binary system, wherein the binary system is formulated into pullulan-based lyophilized tablets.

2. The pharmaceutical composition according to claim 1, wherein said polyvinyl pyrrolidine is polyvinyl pyrrolidone vinyl acetate.

3. The pharmaceutical composition according to claim 1, wherein the polyvinyl pyrrolidone has an average molecular weight of from 25,000 to 3,000,000.

4. The pharmaceutical composition according to claim 1, wherein the at least one excipient comprises one or more of a binder, a filler, a sweetener, a swelling-aid polymer, a wetting aid, and a disintegrant.

5. The pharmaceutical composition according to claim 4, wherein at least one excipient comprises hydroxylpropyl methylcellulose (HPMC), aspartame, xylitol and 1-ethenylpyrrolidin-2-one.

6. The pharmaceutical composition of claim 1, wherein the pharmaceutical composition comprises,
   a lyophilized mixture of
      vinpocetine and polyvinyl pyrrolidine vinyl acetate,
      pullulan
      hydroxylpropyl methylcellulose (HPMC),
      aspartame,
      xylitol, and
      1-ethenylpyrrolidin-2-one.

7. A tablet suitable for dissolution in the buccal cavity, comprising:
   a binary system of vinpocetine and at least one polyvinyl pyrrolidone, and
   a pullulan filler.

8. The tablet of claim 7, wherein the tablet has a thickness of about 3.50 to 5.50 mm.

9. The tablet of claim 8, wherein the tablet has a weight of about 105 to 180 mg.

10. A method of treating a cerebral degenerative disease in a subject in need thereof, comprising
    administering through the buccal cavity of the subject one or more pullulan-based lyophilized tablets containing a physically modified vinpocetine binary system to treat the cerebrovascular disorder in the subject.

11. The method of claim 10, wherein the cerebral degenerative disease is Alzheimer's disease.

12. The method of claim 10 wherein the physically modified vinpocetine binary system comprises vinpocetine and a polyvinyl pyrrolidone.

13. The method of claim 12 wherein the polyvinyl pyrrolidone is polyvinyl pyrrolidone acetate.

14. The method of claim 10, wherein the one or more pullulan-based lyophilized tablets comprise 5-15% w/w pullulan.

* * * * *